United States Patent [19]

Mauvernay et al.

[11] 4,011,240
[45] Mar. 8, 1977

[54] SUBSTITUTED CYSTEINES

[75] Inventors: Roland-Yves Mauvernay, Riom; André Monteil, Gerzat; Jacques Simond, Chamalieres; Jacques Moleyre, Mozac; Norbert Busch, Loubeyrat, all of France

[73] Assignee: Centre Europeen de Recherches Mauvernay (CERM), Riom, France

[22] Filed: Oct. 12, 1972

[21] Appl. No.: 296,902

[30] Foreign Application Priority Data

Oct. 13, 1971 France .............................. 71.36840

[52] U.S. Cl. ...................... 260/332.2 A; 260/516; 424/275; 424/317
[51] Int. Cl.² ........................................ C07D 333/16
[58] Field of Search ............ 260/332.2 A, 516, 519

[56] References Cited

UNITED STATES PATENTS 3,479,402  11/1969  Cragoe .............................. 260/520
3,634,365  1/1972  Roberts et al. .................... 260/78 A

OTHER PUBLICATIONS

Jones, et al., Can. J. Chem., 1971, 49(18), 3012–3019.
Glasel, et al., Arch. Biochem. Biophys. 115(2), 237–246 (1966).
Erlanger, et al., J. Biol. Chem. 240:PC3447–8 (1965).

Primary Examiner—Henry R. Jiles
Assistant Examiner—C. M. S. Jaisle

[57] ABSTRACT

This invention relates to a new group of substituted cysteines having the general formula:

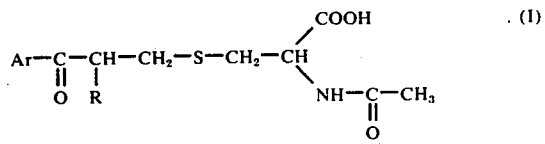

in which:
Ar is an aromatic or heteromonocyclic group, such as 2-thienyl or phenyl, which may be substituted by a halogen atom or by a lower alkyl or alkoxy group, and R is a hydrogen atom or a lower alkyl group.

These compounds are of use in human therapeutics as liquifiers for bronchal secretions in complaints of the respiratory passage and, in particular, in chronic bronchitis.

The invention also relates to a method of preparing these compounds and to the application of these compounds, particularly in human therapeutics.

3 Claims, No Drawings

SUBSTITUTED CYSTEINES

This method of the invention constitutes an application of the conventional method of obtaining thio ethers by the reaction between a beta-aminoketone and a mercaptan. In the present case the mercaptan is N-acetylcysteine, and the beta-aminoketone has the general formula $$Ar-CO-CHR-CH_2-N(CH_3)_2 \qquad (II)$$

in which Ar and R are as defined above.

Such amino ketones may be obtained by known methods which are described, for example, by H. Weyl (Methoden der Organischen Chemie, Volume 2, No. 1, pages 731 to 795) and B. Reichert (Die Mannich Reaktion, Springer Verlag, 1959).

In carrying out this method, one mole of the beta-aminoketone and 1.1 mole of N-acetylcysteine are dissolved in ethyl acetate and heated for five to six hours after distillation of the solvent. Completion of the reaction is checked by thin-layer chromatography.

The reaction proceeds as follows:

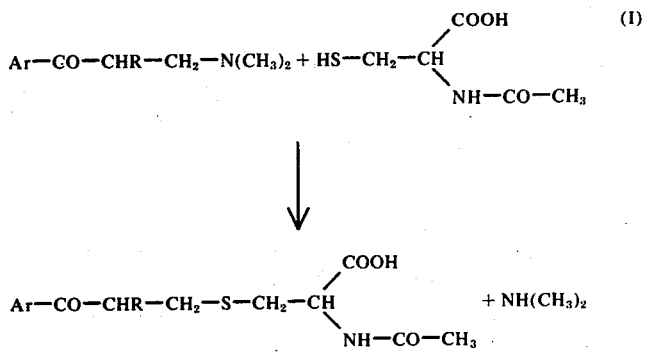

Nine compounds according to the present invention and their characteristic features are listed in the appended Table I by way of example.

TABLE I

| Compound No. | Substituents R | Substituents Ar | Melting point | Acidimetric determination | Analysis | N | C | H |
|---|---|---|---|---|---|---|---|---|
| 1 | CH₃ | 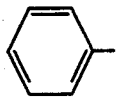 | 90–91° C | 98% | Theory %<br>Found % | 4.52<br>4.57 | 58.23<br>57.84 | 6.19<br>6.11 |
| 2 | H | 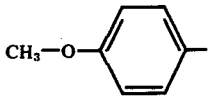 CH₃—O— | 145.5° C | 96% | Theory %<br>Found % | 4.30<br>4.38 | 55.37<br>56.49 | 5.88<br>5.62 |
| 3 | H | 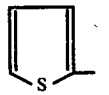 | 141.5° C | 99% | Theory %<br>Found % | 4.65<br>4.66 | 47.82<br>48.71 | 5.01<br>5.03 |
| 4 | H | 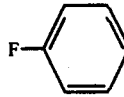 F— | 117.5° C | 98% | Theory %<br>Found % | 4.47<br>4.49 | 53.66<br>54.72 | 5.14<br>5.03 |
| 5 | H | 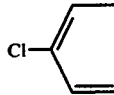 Cl— | 138.4° C | 99% | Theory %<br>Found % | 4.25<br>4.24 | 50.98<br>52.0 | 4.89<br>4.79 |
| 6 | H | 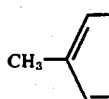 CH₃— | 157.5° C | 97% | Theory %<br>Found % | 4.52<br>4.56 | 58.23<br>59.3 | 6.19<br>5.81 |
| 7 | H | 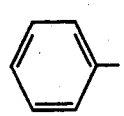 | 148° C | 97% | Theory %<br>Found % | 4.74<br>4.73 | 56.93<br>57.39 | 5.8<br>5.4 |

TABLE I-continued

| Compound No. | R | Ar | Melting Point | Acid function | N | C | H |
|---|---|---|---|---|---|---|---|
| 8 | CH₃ | Cl—⟨phenyl⟩— | 124° C | 98% | Theory % 4.07<br>Found % 4.10 | 52.39<br>53.82 | 5.27<br>5.19 |
| 9 | CH₃ | CH₃O—⟨phenyl⟩— | 125.4° C | 97% | Theory % 4.12<br>Found % 4.17 | 56.61<br>55.83 | 6.29<br>5.86 |

The following examples illustrate the preparation of compounds according to the invention : these examples are for the preparation of two of the compounds shown in Table I :

EXAMPLE 1

Preparation of
N-acetyl-S-(3-phenyl-3-oxo-2-methyl)propylcysteine
(Compound No. 1)

19.2g (0.1M) of N,N-dimethyl-(3-phenyl-3-oxo)-propylamine and 14.8g (0.11M) of N-acetyl-L-cysteine are dissolved in 50 ml of ethyl acetate. The solvent is distilled and the residue is heated for six hours on a boiling water bath.

The doughy mass obtained is dissolved in an aqueous solution of sodium carbonate. This solution is washed with ether, then acidified with cold concentrated hydrochloric acid.

The precipitate obtained is recrystallized from 96° ethanol. There are thus obtained 23g of a product (yield~75%) having a melting point of 90°–91° C.

| Analysis: | Acidimetric determination:98% of the theoretical | | |
|---|---|---|---|
| | C % | H % | N % |
| Calculated | 58.23 | 6.19 | 4.52 |
| Found | 57.84 | 6.11 | 4.57 |

EXAMPLE II

Preparation of
N-acetyl-S-(3-phenyl-3-oxo)propylcysteine
(Compound No. 7).

18g (0.1M) of N,N-dimethyl-(3-phenyl-3-oxo)-propylamine and 14.8g (0.11M) of N-acetyl-L-cysteine are reacted under the same conditions as those described above in Example I.

20g of product are obtained (yield~68%) having a melting point of 148° C. Acidimetric determination : 97% of the theoretical

| Analysis | Acidimetric determination : 97% of the theoretical | | |
|---|---|---|---|
| | C % | H % | N % |
| Calculated | 56.93 | 5.8 | 4.74 |
| Found | 57.39 | 5.4 | 4.73 |

The compounds of the present invention have significant mucolytic properties which enable them to be used in human therapeutics. An an example, the results obtained with compound No. 1 are reported below.

DETAILS OF EXPERIMENT

The action of Compound No. 1 on the viscosity of sputum was examined in vitro. The measurements were performed using a Brookfield conical plate micro-viscosimeter. This enables the breaking effect exerted upon a rotor which turns at a constant, predetermined speed to be measured. The rotor is immersed in a liquid the viscosity of which it is desired to measure.

Measurements are performed as follows : 1.5 ml of secretion brought to ambient temperature are poured into the receptacle of the viscosimeter. After four minutes the temperature of the sputum in the receptacle is constant at 37° C and its viscosity is measured. Then, proceeding in the same way the viscosity of a specimen of the sputum to which a drop of solvent has been added is measured. The values obtained are used as control values.

1.5 ml of secretion are then taken from the same spittoon to which is added a drop of a solution prepared from the substance under test and the solvent referred to above. (The solution is produced in such a manner as to obtain a concentration of the substance under test in the secretion corresponding to the values indicated in table II). The viscosity of the preparation is measured in the manner described above.

From the values determined by the viscosimeter, the results are expressed as percentage viscosity reduction by a calculation of paired series.

Measurements were carried out at the following concentrations expressed as mg of substance under test per ml of spittle: 3.16 mg/ml, 6.33 mg/ml, 12.66 mg/ml, 19 mg/ml.

Three speeds of rotation of the rotor were used for each concentration viz:- 1.5 rpm, 3 rpm, 6 rpm.

The results obtained are summarized in the following table :

TABLE II

| Speed of rotation | Concentration of the test product in mg per ml of spittle | | | |
|---|---|---|---|---|
| | 3.16 | 6.33 | 12.66 | 19 |
| 6 rpm | 26% | 36% | 49% | 67% |
| 3 rpm | 16% | 31% | 42% | 61% |
| 15 rpm | 9% | 30% | 44% | 61% |

From the foregoing, it can be seen that the products according to the present invention may be used with advantage in human therapeutics as liquifiers for bronchial secretions in complaints of the respiratory passages such as chronic bronchitis. The products are to be administered orally (tablets, syrup, aerosol) in a daily dose of 1 to 1.5g.

What we claim is:

1. N-acetyl-S-(3-paramethoxyphenyl-3-oxo) propylcysteine.
2. N-acetyl-S-(3-thien-2-yl-3-oxo) propylcysteine.
3. N-acetyl-S-(3-paramethoxyphenyl-3-oxo-2-methyl) propylcysteine.

* * * * *